United States Patent

Trott

Patent Number: 5,851,208
Date of Patent: Dec. 22, 1998

[54] ROTATABLE SURGICAL BURR

[75] Inventor: A. Frank Trott, Largo, Fla.

[73] Assignee: Linvatec Corporation, Largo, Fla.

[*] Notice: This patent issued on a continued prosecution application filed under 37 CFR 1.53(d), and is subject to the twenty year patent term provisions of 35 U.S.C. 154(a)(2).

[21] Appl. No.: 732,539

[22] Filed: Oct. 15, 1996

[51] Int. Cl.$^6$ .................................................. A61B 17/56
[52] U.S. Cl. .................................................. 606/80
[58] Field of Search ................................ 606/79, 80, 81, 606/82, 83, 84, 85, 86, 180, 167

[56] References Cited

U.S. PATENT DOCUMENTS

| 1,677,337 | 7/1928 | Grove . | |
|---|---|---|---|
| 3,082,805 | 3/1963 | Royce . | |
| 3,232,151 | 2/1966 | Blachowski . | |
| 4,141,225 | 2/1979 | Varner . | |
| 4,445,509 | 5/1984 | Auth . | |
| 4,466,429 | 8/1984 | Loscher et al. | 606/80 |
| 4,541,423 | 9/1985 | Barber | 606/80 |
| 4,646,738 | 3/1987 | Trott . | |
| 4,706,659 | 11/1987 | Matthews et al. . | |
| 4,842,578 | 6/1989 | Johnson et al. . | |
| 4,917,085 | 4/1990 | Smith . | |
| 5,069,569 | 12/1991 | Lieser . | |
| 5,100,426 | 3/1992 | Nixon . | |
| 5,135,483 | 8/1992 | Wagner et al. . | |
| 5,152,744 | 10/1992 | Krause et al. . | |
| 5,286,253 | 2/1994 | Fucci . | |
| 5,320,635 | 6/1994 | Smith . | |
| 5,322,505 | 6/1994 | Krause et al. . | |
| 5,366,468 | 11/1994 | Fucci et al. . | |
| 5,391,170 | 2/1995 | McGuire et al. . | |
| 5,403,317 | 4/1995 | Bonutti . | |
| 5,405,348 | 4/1995 | Anspach, Jr. et al. . | |
| 5,411,514 | 5/1995 | Fucci et al. . | |
| 5,423,799 | 6/1995 | Shiu . | |
| 5,489,291 | 2/1996 | Wiley . | |
| 5,522,829 | 6/1996 | Michalos . | |
| 5,527,316 | 6/1996 | Stone et al. . | |
| 5,529,580 | 6/1996 | Kusunoki et al. . | |
| 5,556,408 | 9/1996 | Farhat . | |
| 5,593,416 | 1/1997 | Donahue | 606/170 |
| 5,620,447 | 4/1997 | Smith et al. | 606/79 |

FOREIGN PATENT DOCUMENTS

| 2 220 729 | 1/1990 | United Kingdom . |
|---|---|---|
| WO 92/15255 | 9/1992 | WIPO . |

Primary Examiner—Guy V. Tucker
Attorney, Agent, or Firm—Gene Warzecha

[57] ABSTRACT

An elongated, rotatable surgical cutting instrument having a rotatable cutting element at the distal end of a bendable non-rotating elongated outer member. The instrument enables operation of various cutting devices such as a bendable rotatable burr. In one embodiment the cutting element is rotatably, but irremovably attached to the distal end of the outer member. The proximal end of the cutting element is then releasably attached to the distal end of a flexible coupling which in turn is attached to the distal end of an elongated inner member. The assembly is then rotatably secured within the outer member so the cutting element may be rotated via the inner member. An aspirating lumen extends through the cutting element, the flexible coupling and the inner member and the inner member may be removed from the outer member without detaching the cutting element therefrom. In another embodiment, the cutting element is removable from the outer member when the inner member is removed.

3 Claims, 7 Drawing Sheets

ROTATABLE SURGICAL BURR

BACKGROUND OF THE INVENTION

1. Field of the Invention

The invention relates to a rotatable surgical cutting instrument powered by a drive motor within a handpiece. More particularly, the invention relates to an elongated rotatable inner member rotatably situated within an elongated outer member, the inner member having one or more cutting edges at its distal tip. The invention also relates to a bendable device in which the distal tips of the inner and outer member may be situated at a predetermined angle relative to the axis of the proximal ends of the members.

2. Description of the Prior Art

The use of elongated surgical cutting instruments has become well accepted in performing closed surgery such as arthroscopic or, more generally, endoscopic surgery. In closed surgery, access to the surgical site is gained via one or more portals, and instruments used in the surgical procedure must be elongated to permit the distal ends of the instruments to reach the surgical site. Surgical cutting instruments for use in close surgery —also known as "shavers"— conventionally have a straight, elongated outer tubular member terminating at a distal end having an opening in the end or side wall (or both) to form a cutting port or window and a straight, elongated inner tubular member concentrically disposed in the outer tubular member and having a distal end disposed adjacent the opening in the distal end of the outer tubular member. The distal end of the inner tubular member has a surface or edge for engaging tissue via the opening in the distal end of the outer tubular member and in many cases (but not all) cooperates with the opening to shear, cut or trim tissue. In some cases, such as burrs, the opening in the outer tube merely allows the inner member access to the tissue and does not otherwise cooperate with the inner member. The inner tubular member is rotatably driven about its axis from its proximal end, normally via a handpiece having a small electric motor which is controlled by finger actuated switches on the handpiece, a foot switch or switches on a console supplying power to the handpiece. The distal end of the inner tubular member can have various configurations depending upon the surgical procedure to be performed, and the opening in the distal end of the outer tubular member has a configuration to cooperate with the particular configuration of the distal end of the inner tubular member. Cut tissue is aspirated through the hollow lumen of the inner tubular member to be collected via a vacuum tube communicating with the handpiece.

With the continuing expansion of endoscopic surgery into different parts of the body, the limitations of existing devices become apparent and necessitate the invention of new and unique instruments. Thus it is that as surgeons become more adept at performing arthroscopic and endoscopic surgery through natural or artificial portals in the body new instruments become devised to not only facilitate the performance of conventional procedures but to enable the performance of new procedures.

One such development of new endoscopic instruments relates to the improvement of traditional arthroscopic shavers by producing them in pre-bent or bendable forms. An example of a pre-bent or fixed angle endoscopic shaver is shown in U.S. Pat. No. 4,646,738 (Trott) and an example of a bendable, variable angle endoscopic shaver is shown in U.S. Pat. No. 5,411,514 (Fucci et al.), both of these patents assigned to the assignee hereof and incorporated by reference herein.

While pre-bent or bendable shavers are available in the form of shaver blades, the use of pre-bent or bendable burrs would be a benefit in certain applications. However, the way rotatable burrs are used produces some design concerns which have not heretofore been addressed. Because rotatable burrs have elongated burr tips, the lateral forces encountered during use of rotatable burrs tends to urge the distal tip of the burr laterally. In straight, non-bendable burrs this is not detrimental since the burr tip is welded to the distal end of the inner member to produce a strong junction which resists the lateral forces. In a bendable device, however, the junction of the burr tip would be at the distal end of a flexible coupling section. Regardless of the longitudinal and torsional strength of this junction, the flexibility of the coupling section (or the inner member itself if there is no discrete coupling section) could permit the lateral forces to cause the axis of the burr tip to become misaligned with the axis of the inner member at the junction point. This deviation off-axis could make the burr "chatter" and bounce and be generally uncontrollable.

Since known rotatable burrs have burr tips attached to the distal ends of tubular inner members, bendability produces some other design considerations. One practical limitation on the use of bendable burrs is that the distal tip of the burr is attached to the rotatable inner member and is exposed to the ambient. Consequently, for safety purposes the design must be such that the burr tip cannot become easily disengaged from the body of the tubular inner member. The necessary flexibility of the inner member makes it important to strengthen the junction between the burr tip and the inner member. In straight, non-bendable burrs this is easily done by welding or the like but this is not necessarily so easily done in bendable burrs.

Another practical limitation on the use of bendable burrs is that the cutting tip and the inner member may occasionally need to be removed from the outer member in order to unclog the device. Some prior art burrs sometimes have a cutting tip with a larger diameter than the outer member and are generally not removable. If such a device is used on hard tissue such as bone, the clogging problem is almost non-existent because the debris is small enough to be aspirated through the lumen of the inner member. However, in certain applications, for example where the device is used in a dry body cavity as opposed to a fluid filled cavity and/or where the device may be used to cut soft tissue, it would be preferable to design the device for disassembly in order to unclog it if necessary.

While the disassembly of shaver blades is shown, for example, in U.S. Pat. No. 5,320,635 (Smith), the Smith device is unsuitable for end cutting or for use with a burr tip since it teaches that the cutting tip must be captured within a closed outer member having only a window in a side thereof.

It is accordingly an object of this invention to produce a rotatable surgical cutter having a cutting tip selectively attachable to and axially aligned with the rotatable inner member.

It is also an object of this invention to produce a rotatable surgical cutter able to be bent to a predetermined configuration while also able to be disassembled for cleaning purposes.

It is accordingly an object of this invention to produce a rotatable surgical cutter having a cutting tip rotatably attached to the distal tip of the outer member of the cutter and selectively engageable with the distal end of a bendable inner member.

It is an additional object of this invention to produce a rotatable surgical cutter having a rotatable cutting tip attachable to the distal end of a flexible inner member in such a way as to minimize the deviation of the axis of the cutting tip from the axis of the distal end of the inner member when the cutting tip is subjected to a laterally directed force.

SUMMARY OF THE INVENTION

These and other objects of this invention are achieved by the preferred embodiment disclosed herein which is a rotatable surgical cutter for use with a surgical instrument for rotatably driving the cutter. The rotatable cutter comprises an elongated tubular inner member having a proximal end, a distal end, a hollow interior and a hub at the proximal end for attaching the inner member to a source of rotation within the surgical instrument; an elongated tubular outer member having a proximal end, a distal end and a hub at the proximal end for attaching the outer member to the surgical instrument and a cutting tip means axially aligned with the distal end of the outer member for cutting tissue. The cutting tip comprises an elongated member comprising a distal cutting portion, a proximal connecting portion and an intermediate bearing portion. The proximal connecting portion is adapted to releasably engage the distal end of the inner member and the intermediate bearing portion is adapted to enable rotation of the cutting tip means relative to the outer member. All portions of the cutting tip are cannulated to provide aspiration and a flexible coupling section may be interposed in the inner member to produce a bendable device.

In another aspect, the invention lies in the method of producing a rotatable surgical cutter for use with a surgical instrument. The method comprises the steps of providing an elongated tubular inner member having a proximal end, a distal end, an interior lumen and a hub at the proximal end for attaching the inner member to a source of rotation within the surgical instrument. The method further comprises providing an elongated tubular outer member having a proximal end, a distal end and a hub at the proximal end for attaching the outer member to the surgical instrument and attaching to the distal end of the outer member a rotatable cutting element. The method additionally comprises selectively engaging the distal end of the inner member with the proximal end of the cutting element.

DESCRIPTION OF THE PREFERRED EMBODIMENT

Figure 1:
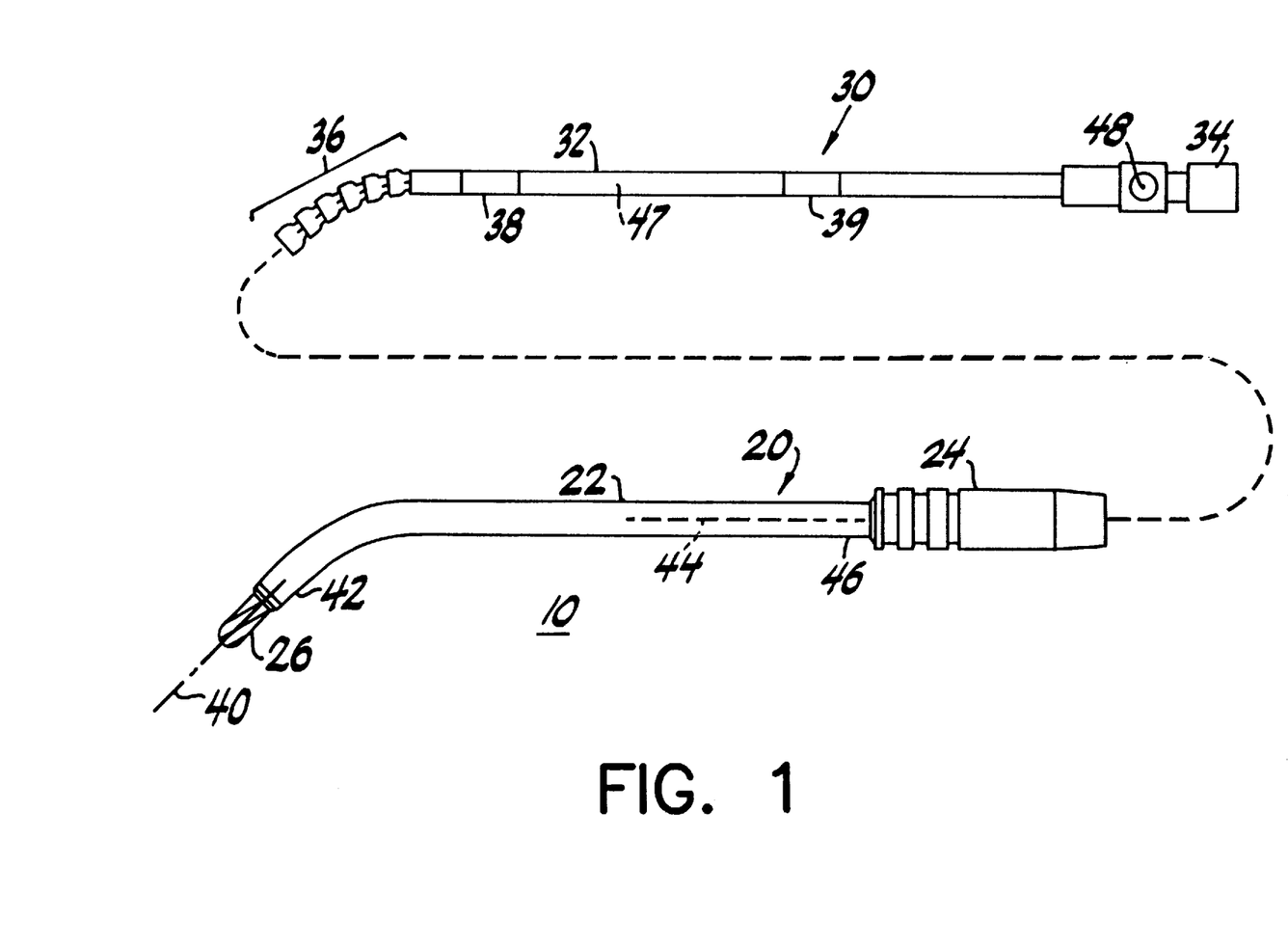
FIG. 1 is an exploded side elevation view of the components of a rotatable surgical cutter constructed in accordance with the principles of this invention.
Figure 2:
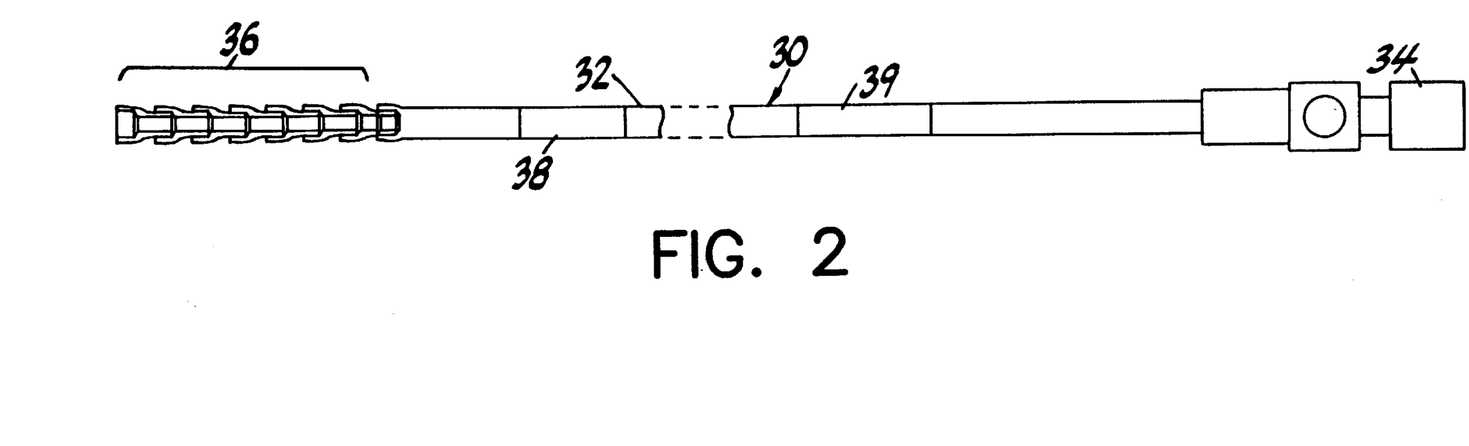
FIG. 2 is a side elevation view of the inner member of the rotatable surgical cutter, partially in cross-section, showing the member in a straightened configuration.
Figure 3:
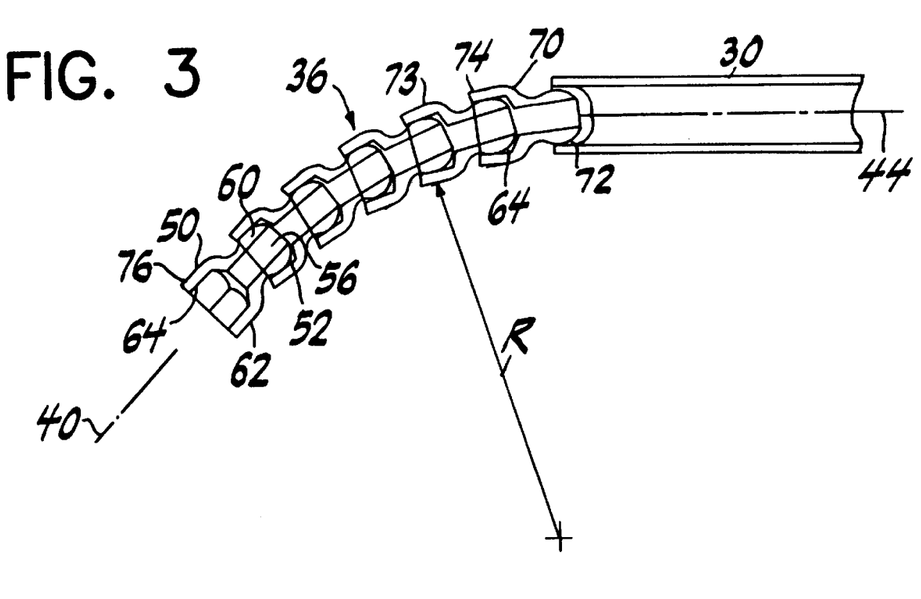
FIG. 3 is a side elevation view, in cross-section, of the flexible coupling portion of the invention.

A rotatable surgical cutter 10 as shown in FIGS. 1–3 comprises an elongated outer member 20 adapted to rotatably receive an elongated hollow inner member 30. Outer member 20 is adapted to be non-rotatably attached to a handpiece (not shown) and comprises an outer tube 22 having a hub 24 at its proximal end and a rotatable burr or other cutting means 26 at its distal end. While the term "cutting" as used herein is intended to mean all types of cutting or resection including burring, shaving, shearing, etc., the preferred embodiment of the invention disclosed herein is a rotatable burr. Inner member 30 comprises an inner tube 32 having a hub 34 at its proximal end and a flexible coupling section 36 at its distal end. The latter enables inner member 30 to operate satisfactorily in either a straight configuration, as shown in FIG. 2, or with any degree of curvature (up to a predetermined maximum as will be understood below) as shown in FIG. 1. A pair of polymeric bearing sleeves 38 and 39 are spaced along tube 32 in a conventional manner. A lumen 47 is produced by the hollow interior of inner tube 32 and communicates with aperture 48 within hub 34 in order to aspirate tissue in a conventional manner. When inner member 30 is properly positioned within outer member 20, the inner hub 34 will be engaged with a rotatable drive motor within the handpiece (not shown).

Outer member 20 may be pre-bent as shown in FIG. 1 in order to have axis 40 of distal end 42 angled a predetermined amount relative to axis 44 of proximal section 46. Alternatively, outer tube 22 may be provided to the user in a straight configuration and may be bent at the surgical site as taught, for example, by the aforementioned U.S. Pat. No. 5,411,514 (Fucci et al.). In either configuration, it will be understood that when the inner and outer members are properly assembled the flexible coupling section 36 will be operatively engaged with rotatable cutting element 26 so that rotation of the inner member 30 will cause rotation of the cutting element while still enabling the inner and outer members 20, 30 to be separated, if necessary.

Figure 4A:
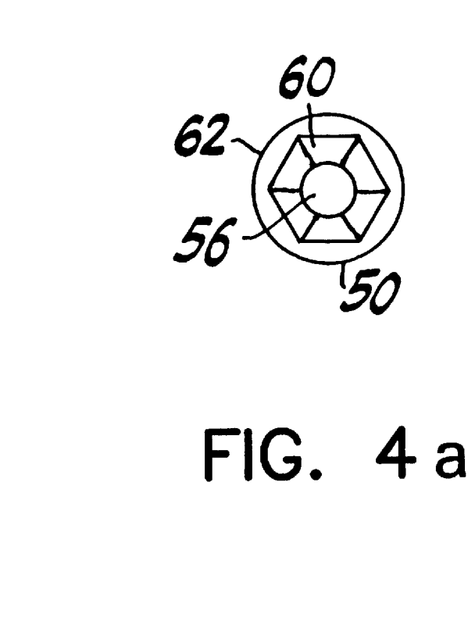
FIGS. 4a, 4b and 4c are left end, side elevation in cross-section and right end views of a link of the flexible coupling shown in FIG. 3.
Figure 4B:
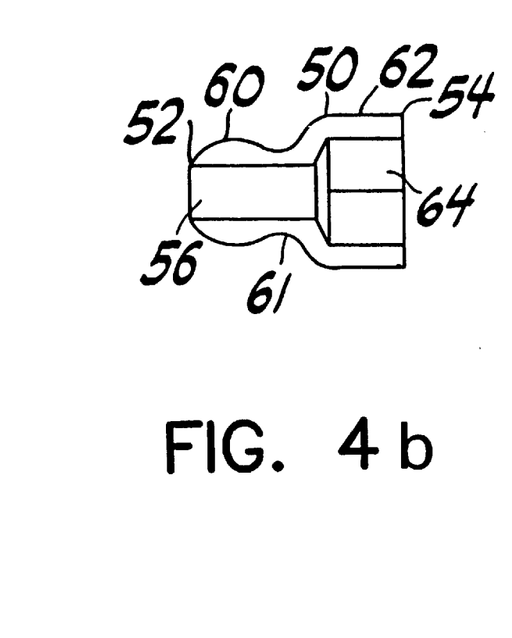
Figure 4C:
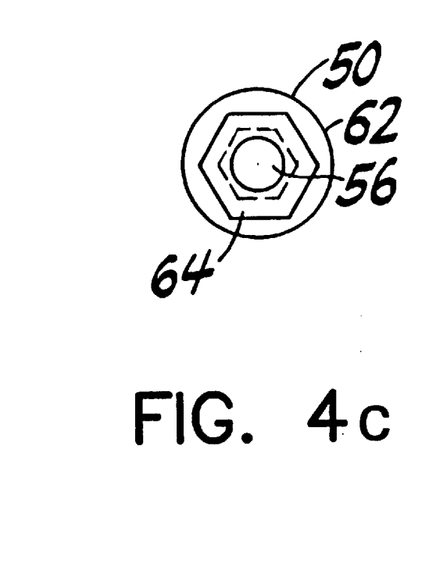

As shown in FIGS. 3 and 4, flexible coupling section 36 comprises a plurality of identical individual links 50 best seen in FIGS. 4a, b and c. Section 36 could be covered with a flexible polymeric sleeve (not shown) as described in U.S. Pat. No. 5,286,253 (Fucci) assigned to the assignee hereof and incorporated by reference herein. Each link 50 has a proximal end 52, a distal end 54 and a throughbore 56. Proximal end 52 has a generally spherical contour comprising a hexagonally segmented structure having longitudinally extending curved hexagonal segments 60 extending from the proximal-most end of the link to neck 61. Distal end 54 has a cylindrical external surface 62 and a hexagonal recess 64. The hexagonal recess 64 of each link is adapted to engage the hexagonal spherical proximal end section 52 of the distally adjacent link as shown in FIG. 3. The proximal-most link 70 is received in the distal end of inner tube 30 in a hexagonally profiled recess 72. The hexagonal recess 64 of link 70 is crimped at 74 in order to engage link 70 to adjacent link 73. The rim at the open end of each hexagonal recess of each link is similarly crimped about the hexagonal spherical projection of the adjacent link throughout the flexible coupling 36. The distal-most link 76, however, has a hexagonal recess 64 which remains uncrimped so that it may be releasably attached to cutting element 26 as will be understood below. Flexible coupling section 36 enables the instrument to operate over a bend radius R which, depending upon the number of links used, may extend even up to 90° between axes 40 and 44. While links 50 are shown oriented so hexagonal recesses face distally, it will be understood that the links could be arranged to have the recesses face proximally.

Figure 5A:
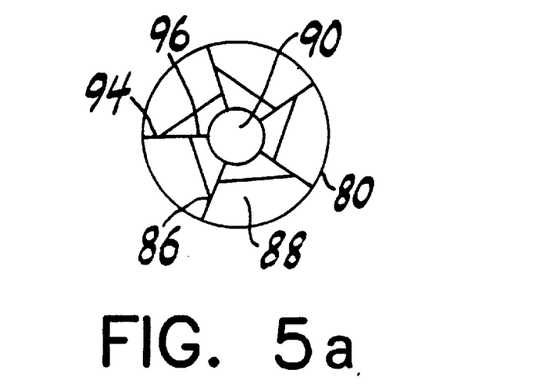
FIGS. 5a, 5b and 5c are left side, side elevation in cross-section and right side views of the distal cutting element shown in FIG. 1.
Figure 5B:
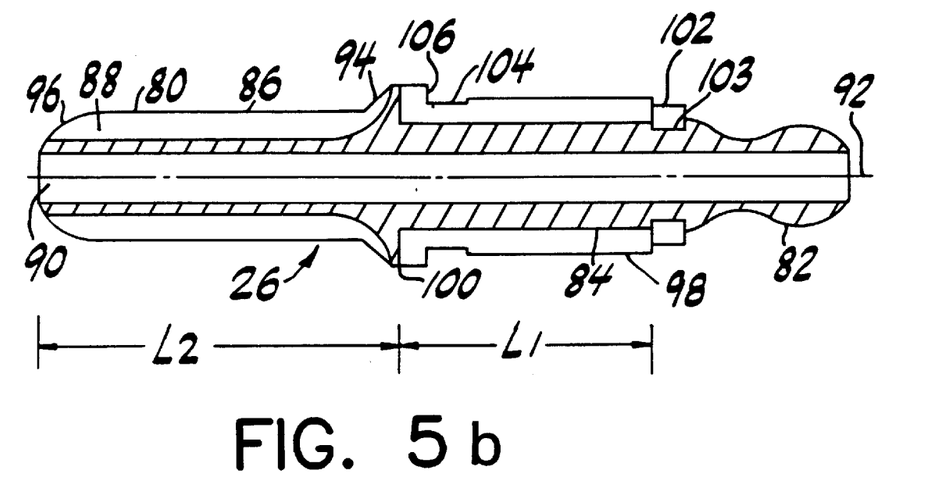
Figure 5C:
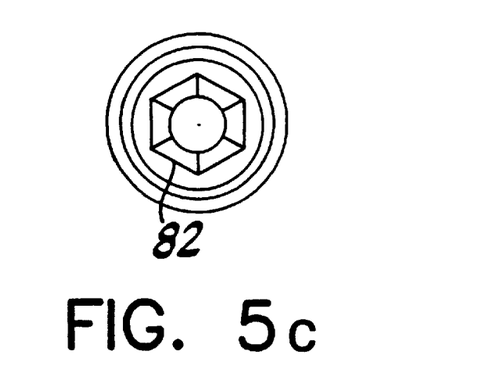

Cutting element 26 as best seen in FIGS. 5a, b and c comprises an elongated distal cutting portion 80, a proximal connecting portion 82 and an intermediate bearing portion 84. Cutting portion 80 comprises a plurality of helical cutting edges 86 and adjacent flutes 88 symmetrically situated about throughbore 90. The number and actual structure of the cutting edges and flutes may vary and some alternate embodiments will be described below. In this embodiment, however, it is noted that the cutting edges are longitudinally extending parallel to axis 92 although the proximal end of each edge 86 may have an end facing cutting portion 94 and the distal portion of each edge 86 has an end facing portion 96. Optimally, the proximal side of cutting portion 80 may simply be flared to eliminate any discrete end-facing cutting portions 94. Each edge 86 is slightly helical in a conventional manner and it will be understood that cutting portion 80 could be formed with a variety of edges (in shape and number) and surfaces to effect a variety of cutting actions. Connecting portion 82 has a spherical hexagonal structure like that of a link portion 50 and is adapted to be detachably received within the uncrimped hexagonal recess 64 of the distal-most link 76. In the preferred embodiment, intermediate bearing portion 84 comprises a cylindrical polymeric bearing 98 held in place adjacent shoulder 100 by bushing 102 received in annular recess 103. Alternatively, a bearing could be provided on the end of the outer member only. Bearing 98 has an annular recess 104 adapted to receive a portion of the distal end of outer tube 22 when the two components are assembled together. It will be understood that securing the cutting element 26 to the distal tip of outer tube 22 allows the cutting element to freely rotate with minimal frictional heat and prevents it from falling out during normal use. Additionally, the distal shoulder 106 of bearing 98 acts as a thrust bearing to enable cutting element 26 to accept longitudinal forces such as would be encountered in end-cutting. In the preferred embodiment, the length L1 is approximately equal to length L2 so the contact of bearing 98 along the inner surface of the outer tube is over a long enough distance to counteract the lateral forces to which cutting portion 86 is subjected.

Figure 6:
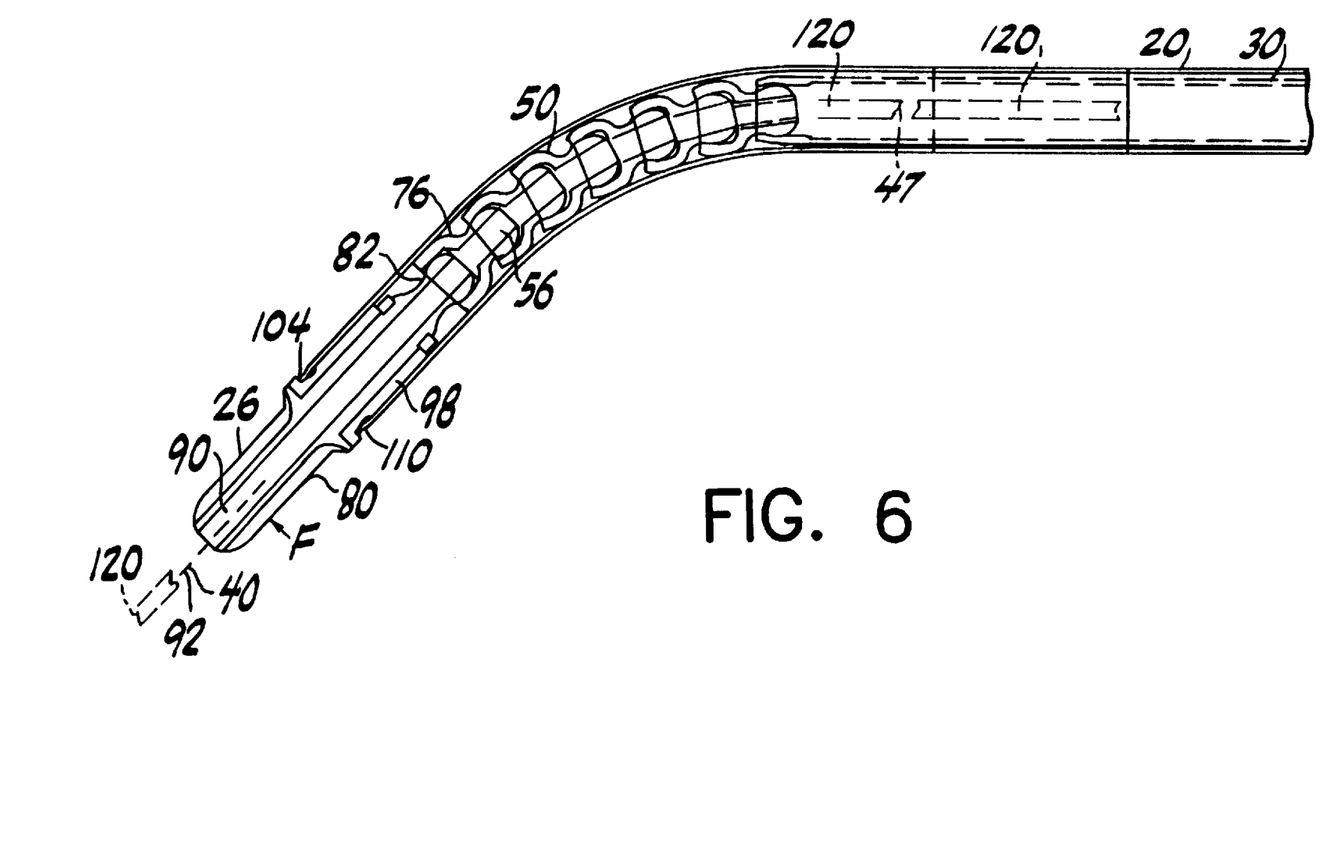
FIG. 6 is a side elevation view in cross-section of the distal end of the inner member of FIG. 1 assembled within the outer member.

As shown in FIG. 6, cutting element 26 is secured to outer tube 20 by crimping or rolling the distal rim 110 into annular recess 104. The inner and outer diameters of outer tube 20, bearing 98 and links 50 are sized appropriately to facilitate manufacture and use. Inserting inner member 30 into outer member 20, even if the latter is bent as shown, will cause the distal-most link 76 to automatically engage connecting element 82 (although a slight rotational movement of the inner member may be necessary if the hexagonal segments are not sufficiently aligned). Thus, inner member 30 will be able to transmit torque from the motor (not shown) to the cutting tip 26. Bearing 84 enables cutting tip 26 to be subjected to lateral force F (from any radial direction) without causing its axis 92 to deviate detrimentally from axis 40 of the distal end of the outer tube 20. Throughbore 90 is aligned with the bores 56 of link 50 and ultimately with the lumen 47 of inner member 30 to allow debris to be aspirated therethrough. If necessary, inner member 30 may be removed from the outer member because the distal link 76 is removably attachable to connecting portion 82.

An additional benefit of the invention is the ability of the device to follow an optional guidewire 120, shown in phantom. The cannulation over its entire length distal of hub 34, formed by the axial communication of bore 90, bores 56 and lumen 47, enables the device to axially receive guidewire 120 and thus be directed to a particular surgical worksite. Depending upon the length of the guidewire, the hub 34 could be modified to fit a Trinkle type coupling (not shown) to allow the guidewire to extend therethrough while enabling rotation of the inner member or, if the guidewire is short enough, the hub could be left unmodified; that is, without having an accommodating throughbore for the guidewire. Depending on the chosen method and hub configuration, the guidewire 120 could be retained in place while the inner member was rotated or the guidewire could be removed after proper placement of the cutter.

Figure 7:
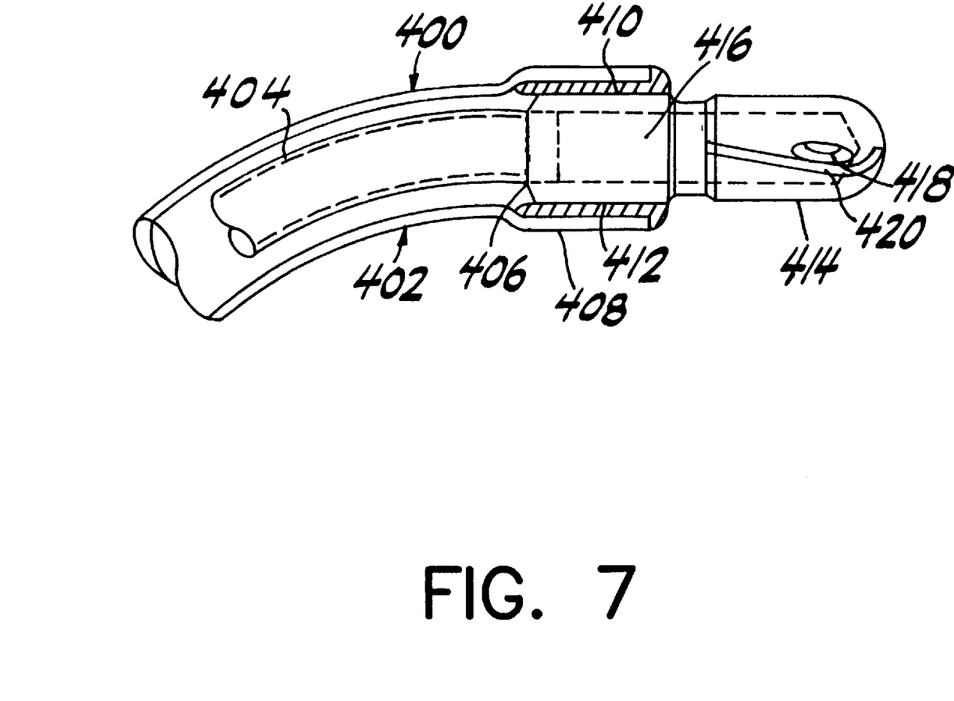
FIG. 7 is an alternate embodiment of the distal end of a rotatable surgical burr.

Another alternate embodiment of the invention is shown in FIG. 7 in which rotatable surgical cutter 400 has an outer member 402 similar to that shown in FIG. 1 although the inner member 404 does not include the link-type flexible coupling section shown above. For example, inner member could have its tube portion formed of a hollow plastic tube or a rigid proximal tube having a distal coiled spring coupling section as shown in the aforementioned U.S. Pat. No. 4,646,738 (Trott). In this configuration, the distal end of the inner member is permanently attached to the proximal end of the cutting element at junction 406. The distal end 408 of the outer member 402 is slightly flared in order to receive an annular bearing member 410 between the inside surface of the end of the outer member and outside surface 412 of cutting element 414. Cutting element 414 has an interior channel 416 communicating with the interior of inner member 404. Access to channel 416 is provided by one or more flutes or ports 418 adjacent cutting edges 420. The inner diameter of outer member 402 and the outer diameter of cutting element 414 are such that the latter may be removed proximally, even past a bent portion of the outer tube, when the inner tube is removed.

Figures 8, 9:
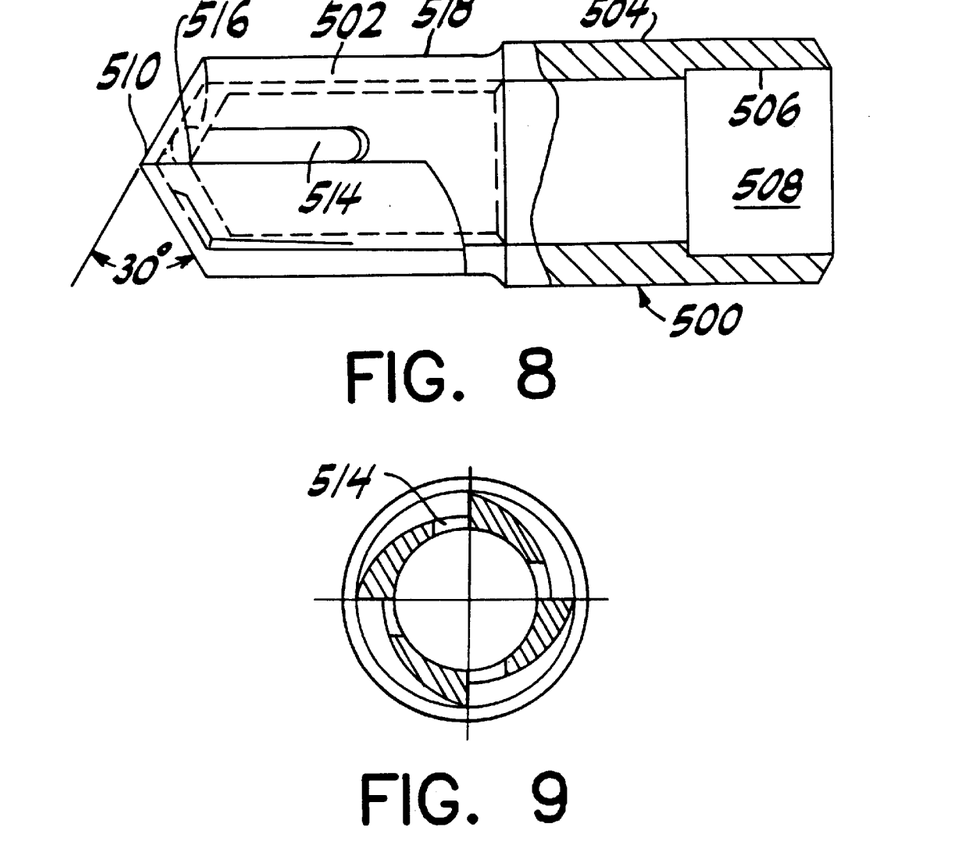
FIGS. 8, 9 and 10 are side elevational, left side and cross-sectional views of an alternate embodiment of the cutting element at the distal end of the rotatable surgical burr.
Figure 10:
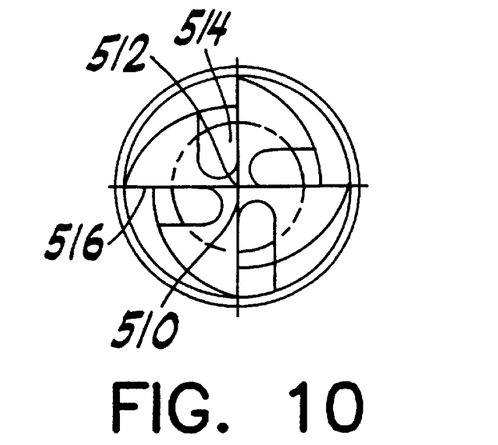

As shown in FIGS. 8–10 an alternate embodiment of the cutting element is shown in the form of cutting element 500 comprising a hollow shell having a cutting portion 502, a bearing portion 504 and connecting portion 506. Bearing portion 504 may be used as in the previously described embodiments. Connecting portion 506 is simply shown diagrammatically as a recess 508 having some (preferably) non-circular cross-section so that it may be joined either directly to the distal end of an inner member (not shown) or to an intermediate connecting member which would then be joined at its other end to the inner member. Cutting portion 502 has a closed distal end in the form of a drill tip 510 having flutes 512 communicating with elongated ports 514. Cutting edges 516 are end-facing and joined at their proximal ends to side-facing cutting edges 518. The shape of cutting portion 502 enables the thickness of the end wall, at drill tip 510, to be approximately equal to the thickness of the side wall, between ports 514, thus enhancing the strength of the structure even if produced with relatively small dimensions (such as a length of 4 mm and a diameter of 3 mm). The plurality of ports integrally formed into the distal end of the shell enables debris to directly pass into the interior of the shell and ultimately the lumen of the inner member (not shown). The placement of the ports in the distal cutting elements of all embodiments disclosed herein facilitates the positioning of the bearing portion of the cutting element closer to the distal end of the outer member than in prior art devices. Cutting element 500 may be removable from the outer member provided the degree of bend of the outer member is not too great (the longer the cutting element, the smaller the bend must be).

It will be understood by those skilled in the art that numerous improvements and modifications may be made to the preferred embodiment of the invention disclosed herein without departing from the spirit and scope thereof.

What is claimed is:

1. A method of producing a rotatable surgical cutter for use with a surgical instrument comprising the steps of:

providing an elongated tubular inner member having a proximal end, a distal end, an interior lumen and a hub at said proximal end for attaching said inner member to a source of rotation within the surgical instrument;

providing an elongated tubular outer member having a proximal end, a distal end and a hub at said proximal end for attaching said outer member to the surgical instrument;

attaching to the distal end of said outer member a cutting element rotatable relative to said outer member and having a distal end and a proximal end;

attaching to the distal end of said inner member a cannulated flexible coupling means for transmitting motion of said inner member to said cutting element, said flexible coupling means having a proximal end, irremovably attached to said distal end of said inner member, and a distal end for engaging the proximal end of said cutting element; and selectively engaging the distal end of said flexible coupling means with the proximal end of said cutting element.

2. A method according to claim 1 further comprising the steps of:

producing a bend in the outer member so that its distal end will be aligned along an axis diverging from the axis of its proximal end;

providing flexible means on said inner member to enable it to transmit torque to said rotatable cutting element past said bend of the outer member.

3. A method of using a surgical instrument having a rotatable surgical cutter comprising the steps of:

providing an elongated tubular inner member having a proximal end, a distal end, an interior lumen and a hub at said proximal end for attaching said inner member to a source of rotation within the surgical instrument;

providing an elongated tubular outer member having a proximal end, a distal end and a hub at said proximal end for attaching said outer member to the surgical instrument;

rotatably attaching to the distal end of said outer member a cutting element rotatable relative to said outer member and having a distal end and a proximal end;

attaching to the distal end of said inner member a cannulated flexible coupling means for transmitting motion of said inner member to said cutting element, said flexible coupling means having a proximal end, irremovably attached to said distal end of said inner member, and a distal end for engaging the proximal end of said cutting element;

selectively engaging the distal end of said flexible coupling means with the proximal end of said cutting element;

providing at least one aperture in said cutting element, said at least one aperture in communication with said interior lumen of said tubular inner member;

providing an aspirating vacuum through said interior lumen of said inner member and said at least one aperture of said cutting element; and rotating said tubular inner member relative to said tubular outer member to thereby rotate said cutting element relative to said outer member while aspirating through said at least one aperture.

\* \* \* \* \*